United States Patent
Matsumoto et al.

(10) Patent No.: US 6,207,711 B1
(45) Date of Patent: Mar. 27, 2001

(54) PHOTOAGING INHIBITOR AND SKIN-CARE PREPARATION

(75) Inventors: Katsuo Matsumoto; Hiroki Tsuruoka; Norio Fujiwara; Yasutomo Nishimori; Yukiko Kenjo, all of Yokohama (JP)

(73) Assignee: Pola Chemical Industries Inc., Shizuoka (JP)

(*) Notice: Subject to any disclaimer, the term of this patent is extended or adjusted under 35 U.S.C. 154(b) by 0 days.

(21) Appl. No.: 09/214,213
(22) PCT Filed: Mar. 17, 1997
(86) PCT No.: PCT/JP97/00847
§ 371 Date: Dec. 22, 1998
§ 102(e) Date: Dec. 22, 1998
(87) PCT Pub. No.: WO98/00093
PCT Pub. Date: Jan. 8, 1998

(30) Foreign Application Priority Data

Jul. 2, 1996 (JP) ................................... 8-172640

(51) Int. Cl.[7] .................................................. A61K 31/215
(52) U.S. Cl. ............................................ 514/552; 424/401
(58) Field of Search ............................. 424/401; 514/552

(56) References Cited

FOREIGN PATENT DOCUMENTS 0 717 983 A1  6/1996  (EP).
8165231 A2  12/1994  (JP).

OTHER PUBLICATIONS

Hashimoto et al., Anti–AIDS Agents. XXVII. Synthesis & Anti HIV Activity of Betulinic Acid & Dihydrobetulinic Acid Derivatives, Bioorg. Med. Chem. 2133–2143, 1997.*
Online Search.*

\* cited by examiner

Primary Examiner—S. Mark Clardy
Assistant Examiner—Michael A. Williamson
(74) Attorney, Agent, or Firm—Knobbe, Martens, Olson & Bear, LLP

(57) ABSTRACT

In order to obtain photoaging inhibitor comprising a triterpenoid compound having high safety and excellent photoaging inhibiting effect, a photoaging inhibitor comprises one or more compounds selected from triterpenoid derivatives and salts thereof, wherein the triterpenoid derivatives are derived by substituting a functional group for a hydrogen atom in a carboxyl group at the 28-position and/or a hydrogen atom in a hydroxyl group bonded to a carbon atom at the 3-position of ursolic, oleanolic or betulic acid, wherein at least one of the functional groups is a functional group having an aromatic ring.

Further, in order to obtain a skin-care preparation excellent in the skin beautifying effect such as inhibiting or ameliorating wrinkled skin effect, a skin-care preparation is blended with one or more compounds selected from triterpenoid derivatives and salts thereof, wherein the triterpenoid derivatives are derived by substituting a functional group for a hydrogen atom in a carboxyl group at the 28-position and/or a hydrogen atom in a hydroxyl group bonded to a carbon atom at the 3-position of ursolic, oleanolic or betulic acid, wherein at least one of the functional groups is a functional group having an aromatic ring, preferably in a content of 0.0001 to 10% by weight.

9 Claims, 3 Drawing Sheets

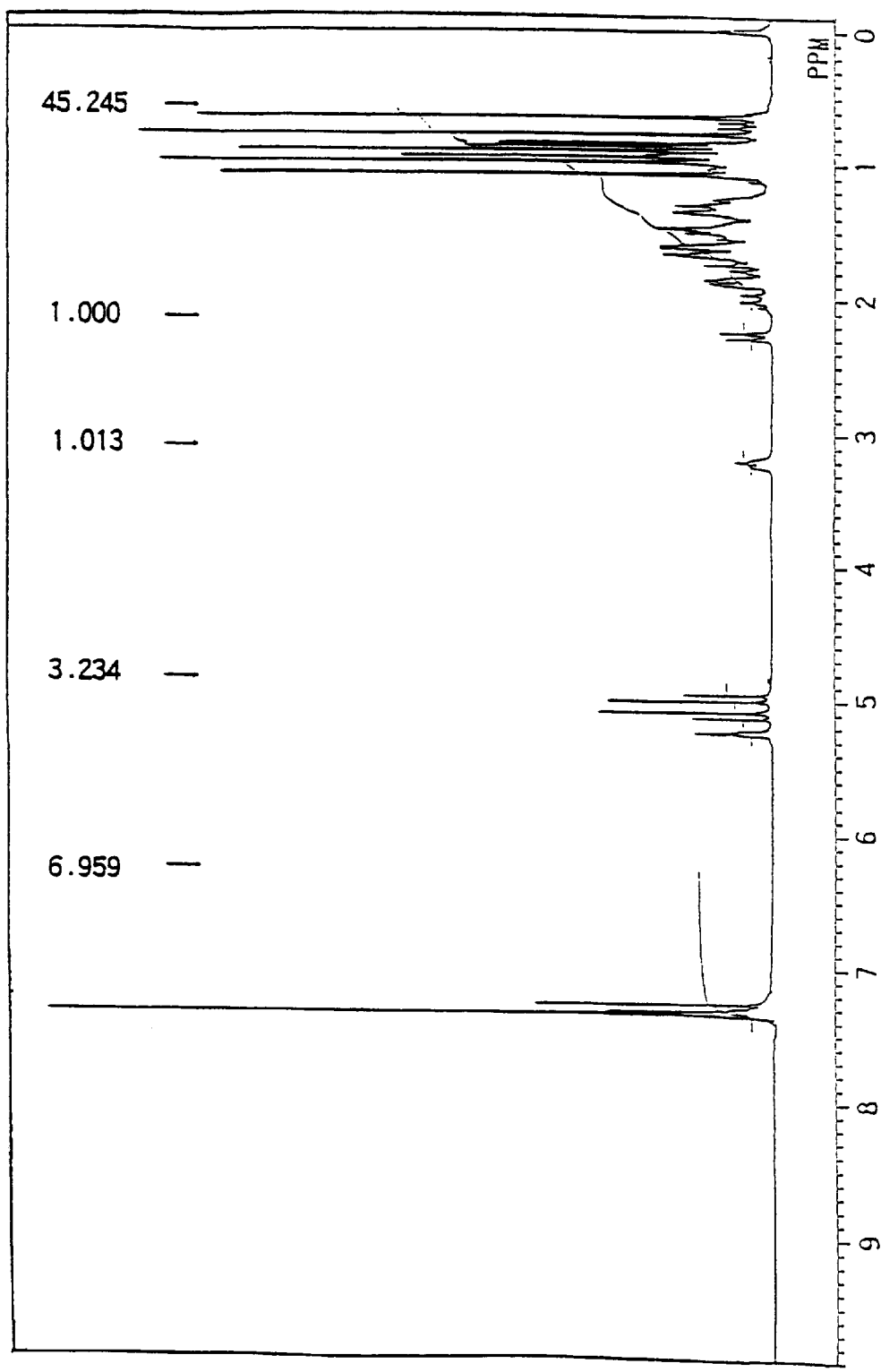
F I G. 1

PHOTOAGING INHIBITOR AND SKIN-CARE PREPARATION

TECHNICAL FIELD

The present invention relates to a photoaging inhibitor and a skin-care preparation and more particularly to a photoaging inhibitor comprising an aromatic compound derivative of triterpenoid and/or salts thereof and to a skin-care preparation which contains an aromatic compound derivative of triterpenoid and/or salts thereof and is excellent in the skin beautifying effect of preventing and ameliorating wrinkled skins.

BACKGROUND ART

Generally, by the term skin aging is meant a physiological phenomenon which involves a physiological aging with getting old and photoaging due to exposure to sunlight (ultraviolet rays) influencing each other. Currently, attention is being paid to relationship between the latter, i.e., photoaging, and wrinkled skin, rough skin, spots, and the like. That is, it has been known that continued exposure to sunlight (ultraviolet rays) increases deep wrinkles in the face or neck and further renders the skin dry and rough, and causes pigment deposition such as spots, freckles, and the like. Therefore, troubles in the skin due to photoaging has become an issue.

Hitherto, in order to prevent the damages to the skin due to ultraviolet rays, cosmetics (sun-screen or sun-protecting cosmetics) containing various ultraviolet absorbents, scattering or shielding agents, such as titanium oxide, zinc oxide, p-methoxycinnamic acid esters, p-aminobenzoic acid esters, and the like, have been developed and put into use. However, it is difficult to protect the skin from abundant exposure to sunlight despite the use of such cosmetics. Further, it has been known that external application of all trans-type retinoic acid is effective as a method of improving the above-described photoaging (see Methods in Enzymology, Vol. 190, p. 352–360 (1990)). However, use of this method is open only to doctors from the viewpoint of safety so that there has been demanded a development of a photoaging inhibitor and skin-care preparations which are highly effective and safe.

Accordingly, in order to meet the above-described demand, there have been used triterpenoids from plant origins, such as ursolic acid and oleanolic acid, or their derivatives such as esters, in photoaging ameliorating agents, cosmetics, externally applied skin agents and the like. However, triterpenes used as raw materials for these substances are very low in their content in plants so that there occur problems that blending them in amounts which assure sufficient effects is expensive and that it is difficult to assure a sufficient supply of them. Therefore, there has been a demand for the development of triterpenoid compounds that can exhibit sufficient effects in small amounts among the triterpenoid compounds which are highly safe, have photoaging preventing and ameliorating effect and are excellent in the skin beautifying effect.

DISCLOSURE OF THE INVENTION

The present invention has been completed from the above-described viewpoints and an object of the present invention is to provide a photoaging inhibitor comprising a triterpenoid compound which is highly safe and excellent in photoaging inhibiting effect and another object of the present invention is to provide a skin-care preparation which is excellent in the skin beautifying effect such as preventing and ameliorating wrinkled skin and the like.

As a result of intensive investigation with a view to solving the above-described problems, the present inventors have found that among triterpenoid derivatives which derived by substituting a functional group for a hydrogen atom in a carboxyl group at the 28-position and/or a hydrogen atom in a hydroxyl group bonded to a carbon atom at the 3-position of ursolic, oleanolic or betulic acid, those which derived by substituting a functional group having an aromatic ring for at least one of the above-described hydrogen atoms (hereafter, sometimes referred to as "aromatic compound derivative of triterpenoid") and salts thereof have a physiological activity by at least 10 times as potent in the effect of inhibiting or ameliorating photoaging of skin as triterpenoids such as ursolic acid, oleanolic acid, and betulic acid, and their aliphatic acyl derivatives and aliphatic ester derivatives hitherto reported and further that skin-care preparations containing the above-described aromatic compound derivative of triterpenoid and/or salts thereof are excellent in the skin beautifying effect such as preventing and ameliorating wrinkled skin and the like, thus completing the present invention.

That is, the present invention provides a photoaging inhibitor comprising one or more compounds selected from triterpenoid derivatives and salts thereof, wherein the triterpenoid derivatives are derived by substituting a functional group for a hydrogen atom in a carboxyl group at the 28-position and/or a hydrogen atom in a hydroxyl group bonded to a carbon atom at the 3-position of ursolic, oleanolic or betulic acid, wherein at least one of the functional groups is a functional group having an aromatic ring.

As the compound which can be used as the photoaging inhibitor of the present invention is specifically those in which the functional group having an aromatic ring is a group represented by general formula (I) below when it is a substituent group for the hydrogen atom in the carboxyl group at the 28-position, or a group represented by general formula (I) or (II) below when it is a substituent group for the hydrogen atom in the hydroxyl group bonded to the carbon atom at the 3-position:

wherein, in the above formula (I), $R_1$ represents a substituted or unsubstituted aromatic ring, and $R_2$ represents a hydrogen atom or a substituted or unsubstituted aromatic ring,

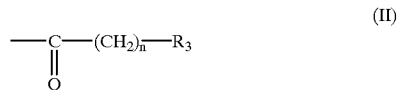

wherein, in the above formula (II), $R_3$ represents a substituted or unsubstituted aromatic ring, and n represents 0 or an integer of up to 2.

More specific compounds include those triterpenoid derivatives and salts thereof, wherein in the general formula (I), the $R_1$ represents a phenyl group, a methoxyphenyl group, an ethoxyphenyl group, a butoxyphenyl group, a nitrophenyl group, a diphenyl group, or a naphthyl group and $R_2$ represents a hydrogen atom or a phenyl group, and the $R_3$ in the general formula (II) represents a phenyl group, a methoxyphenyl group, an ethoxyphenyl group, a butoxyphenyl group, a nitrophenyl group, a diphenyl group, or a naphthyl group.

Further, the present invention provides a skin-care preparation containing one or more compounds selected from triterpenoid derivatives and salts thereof, wherein the triterpenoid derivatives are derived by substituting a functional group for a hydrogen atom in a carboxyl group at the 28-position and/or a hydrogen atom in a hydroxyl group bonded to a carbon atom at the 3-position of ursolic, oleanolic or betulic acid, wherein at least one of the functional groups is a functional group having an aromatic ring. The aromatic compound derivative of the triterpenoids and/or salts thereof to be contained in the skin-care preparation specifically include compounds similar to the aromatic compound derivative of the triterpenoids and/or salts thereof that constitute the above-described photoaging inhibitor. A specific example of the content of the aromatic compound derivative of the triterpenoids and/or salts thereof in the skin-care preparation of the present invention is from 0.0001 to 10% by weight based on the total amount of the preparation.

Hereafter, the present invention will be described in detail. First, the photoaging inhibitor of the present invention will be explained.

(1) Photoaging Inhibitor of the Present Invention

The photoaging inhibitor of the present invention comprise one or more compounds selected from triterpenoid derivatives and salts thereof, wherein the triterpenoid derivatives are derived by substituting a functional group for a hydrogen atom in a carboxyl group at the 28-position and/or a hydrogen atom in a hydroxyl group bonded to a carbon atom at the 3-position of ursolic, oleanolic or betulic acid, wherein at least one of the functional groups is a functional group having an aromatic ring.

Ursolic acid, oleanolic acid, and betulic acid, which serve as a starting material for triterpenoid derivatives used in the photoaging inhibitor of the present invention are compounds having respective structures shown in sequence as below, are each a substance belonging to triterpenoid and widely distribute in the plant kingdom.

(Ursolic acid)

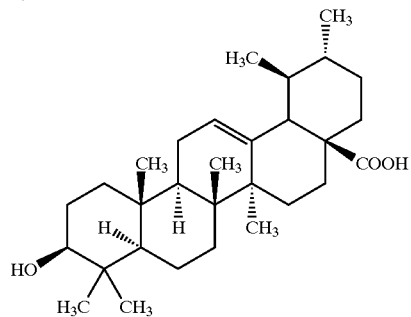

(Oleanolic acid)

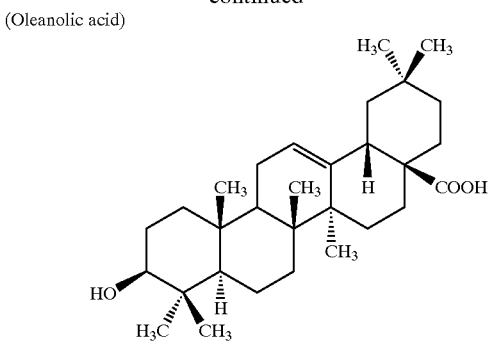

(Betulic acid)

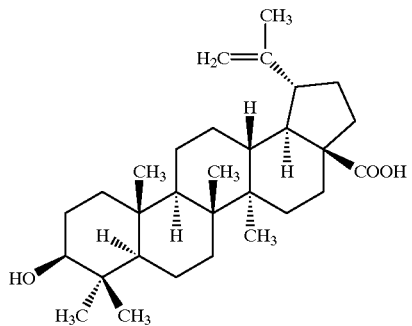

These three triterpenoids can be easily extracted from plants with generally used organic solvents such as alcohols, e.g., methanol, ethanol, etc. However, ursolic acid, oleanolic acid, and betulic acid used in the present invention are not limited to the type of plants from which they have been originated nor to the method by which they have been extracted from plants. Further, in addition to extraction from plants, the triterpenoids can be produced by chemical synthesis and there is no limitation to use of the triterpenoids obtained thereby. Therefore, any suitable methods may be selected for the production method of producing the triterpenoids used as a starting material for the photoaging inhibitor of the present invention taking into consideration economy, safety and the like. Alternatively, commercially available chemicals may be used as a starting material for the photoaging inhibitor of the present invention; for example, ursolic, oleanolic, and betulic acids are commercially available from Tokyo Kasei, Co., Ltd., etc., Wako Pure Chemical Industries, Ltd., etc., and Aldrich Co., etc., respectively.

The triterpenoid derivatives used in the present invention have the structures which are derived by substituting a functional group for a hydrogen atom in a carboxyl group at the 28-position and/or a hydrogen atom in a hydroxyl group bonded to a carbon atom at the 3-position of the above-mentioned three triterpenoids, wherein at least one of the functional groups is a functional group having an aromatic ring. More specifically, the triterpenoid derivatives used in the present invention include those triterpenoid derivatives derived by substituting a functional group having an aromatic ring for the hydrogen atom in the carboxyl group at the 28-position and/or the hydrogen atom in the hydroxyl group bonded to the carbon atom at the 3-position of ursolic, oleanolic or betulic acid; those triterpenoid derivatives derived by substituting an aliphatic functional group for the hydrogen atom in the carboxyl group at the 28-position and by substituting a functional group having an aromatic ring for the hydrogen atom in the hydroxyl group bonded to the carbon atom at the 3-position of ursolic, oleanolic or betulic acid; and those triterpenoid derivatives derived by substituting an aliphatic functional group for the hydrogen atom of the hydroxyl group bonded to the carbon atom at the 3-position and by substituting a functional group having an aromatic ring for the hydrogen atom of the carboxyl group at the 28-position of ursolic, oleanolic or betulic acid.

The triterpenoid derivatives as described above can be used in the present invention. However, among the triterpenoid derivatives, as for the triterpenoid derivatives having the structure which are derived by substituting a functional group having an aromatic ring for at least the hydrogen atom in the carboxyl group at the 28-position, the substituting functional group for the hydrogen atom in the carboxyl group at the 28-position is preferably a group represented by general formula (I) above, while as for the triterpenoid derivatives having the structure which are derived by substituting a functional group having an aromatic ring for at least the hydrogen atom in the hydroxyl group bonded to the carbon atom at the 3-position, the substituting functional group for the hydrogen atom in the hydroxyl group bonded to the carbon atom at the 3-position is preferably a group represented by general formulae (I) or (II). Further, as for the triterpenoid derivatives having the structure which are derived by unsubstituting any functional group or substituting an aliphatic functional group for the hydrogen atom in the carboxyl group at the 28-position, and by substituting a functional group having an aromatic ring for the hydrogen atom in the hydroxyl group bonded to the carbon atom at the 3-position, the substituting functional group for the hydrogen atom in the hydroxyl group bonded to the carbon atom at the 3-position is preferably a group represented by general formula (II) above. These triterpenoid derivatives can be said to be excellent in the effect of preventing or ameliorating the photoaging of skin.

Here, in general formula (I), $R_1$ represents a substituted or unsubstituted aromatic ring, and $R_2$ represents a hydrogen atom or a substituted or unsubstituted aromatic ring and, hence, when the group represented by general formula (I) is used as the above-described substituting group in the triterpenoid derivatives, the group which connects the triterpenoid radical to the aromatic ring is a methylene group or a methyne group. However, replacing the connecting group by an alkylene group or alkenyl group having two or more carbon atoms may result in insufficient photoaging preventing effect. Further, in the present invention, it is preferred that in general formula (I), $R_1$ represents a phenyl group, a methoxyphenyl group, an ethoxyphenyl group, a butoxyphenyl group, a nitrophenyl group, a diphenyl group, or a naphthyl group, and $R_2$ represents a hydrogen atom or a phenyl group.

Also, in general formula (II), $R_3$ represents a substituted or unsubstituted aromatic ring. In the present invention, $R_3$ preferably represents a phenyl group, a methoxyphenyl group, an ethoxyphenyl group, a butoxyphenyl group, a nitrophenyl group, a diphenyl group, or a naphthyl group. As stated above, enumerated are preferred specific examples of the group having an aromatic ring represented by general formula (I) or (II). In this manner, in the present invention, the aromatic rings are preferably those having a ring number of 1 or 2.

Among the triterpenoid derivatives used in the present invention, in those triterpenoid derivatives which are derived by substituting a functional group having an aromatic ring for the hydrogen atom in the hydroxyl group bonded to the carbon atom at the 3-position and by substituting an aliphatic functional group for the hydrogen atom in the carboxyl group at the 28-position of ursolic, oleanolic or betulic acid, examples of the aliphatic functional group include an alkyl group, an alkenyl group, an alkylene group and the like. As for the triterpenoid derivatives used in the present invention, the aliphatic functional group is preferably an alkyl group and further it is preferred that the alkyl group has 1 to 20 carbon atoms, particularly 8 to 20 carbon atoms, from the viewpoint of safety and ease of handling. The alkyl group may be straight or branched chain or cyclic.

Further, in those triterpenoid derivatives which are derived by substituting a functional group having an aromatic ring for the hydrogen atom in the carboxyl group at the 28-position and by substituting an aliphatic functional group for the hydrogen atom in the hydroxyl group bonded to the carbon atom at the 3-position of ursolic, oleanolic or betulic acid, examples of the aliphatic functional group include an alkyl group, an alkenyl group, an alkylene group, an aliphatic acyl group and the like. As for the triterpenoid derivatives used in the present invention, the aliphatic functional group is preferably an alkyl group or an alkylacyl group and further it is preferred that the alkyl portions of them have 1 to 20 carbon atoms, particularly 8 to 20 carbon atoms, similarly to the above. These alkyl portions may be of a straight or branched chain or cyclic.

The triterpenoid derivatives used in the present invention can be produced by commonly used methods, for example, by a method which uses as a starting material ursolic, oleanolic or betulic acid or a triterpenoid derivative obtained by substituting the aliphatic functional group for the hydrogen atom in the carboxyl group at the 28-position or the hydrogen atom in the hydroxyl group bonded to the carbon atom at the 3-position of ursolic, oleanolic or betulic acid, and allows the starting material to react with an aromatic compound by a synthetic reaction in which the hydrogen atom in the carboxyl group at the 28-position and/or the hydrogen atom in the hydroxyl group bonded to the carbon atom at the 3-position contribute(s) to the reaction, more specifically by a method in which the carboxyl group at the 28-position is esterified with a halogenated aromatic compound, a method in which the hydroxyl group bonded to the carbon atom at the 3-position is etherified with an aromatic alcohol or esterified with an aromatic carboxylic acid, or the like.

To produce the triterpenoid derivatives used as the above-described starting material, which are obtained by substituting the aliphatic functional group for the hydrogen atom in the carboxyl group at the 28-position or the hydrogen atom in the hydroxyl group bonded to the carbon atom at the 3-position of ursolic, oleanolic or betulic acid, there can be cited a method in which the carboxyl group at the 28-position of ursolic, oleanolic or betulic acid is esterified with an aliphatic compound, a method in which the hydroxyl group bonded to the carbon atom at the 3-position of the acid is etherified or esterified with an aliphatic compound, and the like. The etherification and esterification can be performed in the same manner as commonly used methods. For example, esterification through the carboxyl group at the 28-position can be performed in the same manner as the esterification reaction of ordinary carboxylic acids, for example, by allowing the above-described triterpenoid to react with a chlorinating agent such as thionyl chloride in a suitable solvent such as chloroform in the presence of a base such as triethylamine to produce a chloride of the triterpenoid, and allowing the chloride to react with a desired aliphatic alcohol such as methanol, ethanol, isopropyl alcohol, butanol, 2-ethylhexyl alcohol, oleyl alcohol, cetanol, stearyl alcohol, etc. in the presence of a base such as triethylamine.

More specifically illustrating the production method of producing the triterpenoid derivatives used in the present invention, for example, in the case where ursolic, oleanolic or betulic acid or the triterpenoid derivative which is obtained by substituting the aliphatic functional group for the hydrogen atom in the hydroxyl group bonded to the carbon atom at the 3-position of the acid is used as a starting material in order to produce the triterpenoid derivative having the structure which is derived by substituting the group represented by general formula (I) above for at least the hydrogen atom in the carboxyl group at the 28-position of the starting material, there can be cited preferably a method in which the above-described starting material is allowed to react in the presence of a polar solvent such as acetone with a desired reagent obtained by adding bromine or chlorine to a methylene or methyne group which is bonded to the aromatic ring.

Also, in the case where ursolic, oleanolic or betulic acid or the triterpenoid derivative which is obtained by substituting the aliphatic functional group for the hydrogen atom in the carboxyl group at the 28-position of the acid is used as a starting material in order to produce the triterpenoid derivative having the structure which is derived by substituting the group represented by general formula (II) above for at least the hydrogen atom in the hydroxyl group bonded to the carbon atom at the 3-position of the starting material, there can be cited preferably a method in which the above-described starting material is allowed to react in the presence of a non-polar solvent such as tetrahydrofuran and a base such as triethylamine with a desired reagent obtained by brominating or chlorinating the carboxyl group of an aromatic carboxylic acid having the structure in which a carboxyl group is bonded to an aromatic ring through an alkylene group having 0 to 2 carbon atoms.

Further, among the triterpenoid derivatives used in the present invention, in those which are derived by substituting the functional group having the aromatic ring for the hydrogen atom in the carboxyl group at the 28-position and by substituting the aliphatic functional group for the hydrogen atom in the hydroxyl group bonded to the carbon atom at the 3-position of ursolic, oleanolic or betulic acid, or in those which are derived by substituting the functional group having the aromatic ring for the hydrogen atom in the hydroxyl group bonded to the carbon atom at the 3-position and by substituting the aliphatic functional group for the hydrogen atom in the carboxyl group at the 28-position of ursolic, oleanolic or betulic acid, there can be used a production method in which the substitution of ursolic, oleanolic or betulic acid with an aromatic functional group is performed before the substitution with an aliphatic functional group is carried out.

Besides the thus produced triterpenoid derivatives used as a photoaging inhibitor, the salts of the triterpenoid derivatives may be employed. The salts of the triterpenoid derivatives may include an ammonium salt, an alkali metal salt, an organic amine salt and the like, which are obtained by reacting the triterpenoid derivatives with inorganic or organic bases.

In addition, the triterpenoid derivatives which are derived by substituting the functional group for the hydrogen atom in the carboxyl group at the 28-position and/or the hydrogen atom in the hydroxyl group bonded to the carbon atom at the 3-position of ursolic, oleanolic or betulic acid, wherein at least one of the functional groups is the functional group having the aromatic ring, and salts thereof are very stable and their preparations do not cause changes with lapse of time such as discoloration, disodoration, and deactivation by decomposition, so that they can be blended in various preparation formulations with stability and ease.

Next, the skin-care preparations of the present invention will be described.

(2) Skin-care Preparations of the Present Invention

The skin-care preparations of the present invention comprises one or more of triterpenoid derivatives which are derived by substituting a functional group for a hydrogen atom in a carboxyl group at the 28-position and/or a hydrogen atom in a hydroxyl group bonded to a carbon atom at the 3-position of ursolic, oleanolic or betulic acid, wherein at least one of the functional groups is a functional group having an aromatic ring, and salts thereof.

The triterpenoid derivatives which are derived by substituting a functional group for a hydrogen atom in a carboxyl group at the 28-position and/or a hydrogen atom in a hydroxyl group bonded to a carbon atom at the 3-position of ursolic, oleanolic or betulic acid, wherein at least one of the functional groups is a functional group having an aromatic ring, and salts thereof (hereinafter referred as "triterpenoid compound") comprised in the skin-care preparations of the present invention are as described in (1) above and the triterpenoid compounds similar to them can be used in the skin-care preparations of the present invention.

A blending amount of the triterpenoid compound in the skin-care preparations of the present invention is preferably from 0.0001 to 10% by weight, more preferably from 0.001 to 1% by weight, based on the total amount of the preparation. If the blending amount of the triterpenoid compound to the skin-care preparation is less than 0.0001% by weight, the skin beautifying effect like an effect of ameliorating the skin condition such as wrinkled skin may be insufficient while use of the blending amount of above 10% by weight may result in failure of giving the effect which corresponds to an increment in the proportion.

The type of formulation of the preparation of the present invention is not limited particularly but there can be cited, for example, cream, emulsion, oil, lotion, pack, aqueous gel, oil gel and ointment. From the viewpoint of absorption, cream, emulsion, oil and the like are more preferred formulations. These skin-care preparations can be produced in the same manner as conventional skin-care preparations except that the triterpenoid compound is selected and blended appropriately depending on the type of formulation.

In addition to the triterpenoid compound, the skin-care preparations of the present invention may contain one or more of suitably selected ones from various components usually used in skin-care preparations, that is, hydrocarbons such as liquid paraffin, vaseline, and squalane; esters such as isopropyl myristate (IPM), synthetic spermaceti, jojoba oil, and carnauba wax; animal and plant fats and oils such as olive oil and beef tallow; higher alcohols such as cetanol and stearyl alcohol; higher fatty acids such as stearic acid and oleic acid; surfactants including anionic surfactants such as sodium lauryl sulfate and alkylsulfosuccinic acid ester, cationic surfactants such as quaternary alkylamine salt, nonionic surfactants such as fatty acid monoglyceride and polyoxyethylene hardened castor oil, and amphoteric surfactants such as alkylbetaine; polyvalent alcohols such as glycerol and propylene glycol; lower alcohols such as ethanol and propanol; preservatives such as paraben and chlorhexidine gluconate; ultraviolet-absorbing agents such as paraaminobenzoic acid derivative and benzophenone derivative; antioxidants such as vitamin E and butylhydroxytoluene; thickeners such as gum arabic and carboxyvinylpolymer; humectants such as polyethylene glycol; pH adjusting agents such as citric acid salt and acetic acid salt;

powders such as titanium oxide, silica gel, and talc; perfumes; dyes; medicinal components in response to various objects such as hyaluronic acid, placenta extract, ginseng extract, vitamins, and sterol glucoside; and the like.

BRIEF DESCRIPTION OF THE DRAWINGS

FIG. 1 is a chart illustrating results of $^1$H-NMR measurement of benzyl ursolate obtained in Production Example 1.

BEST MODE FOR CARRYING OUT THE INVENTION

Hereafter, examples of the present invention will be described. First, production examples of the triterpenoid compounds used in the present invention will be described.

PRODUCTION EXAMPLE 1

Figure 2:
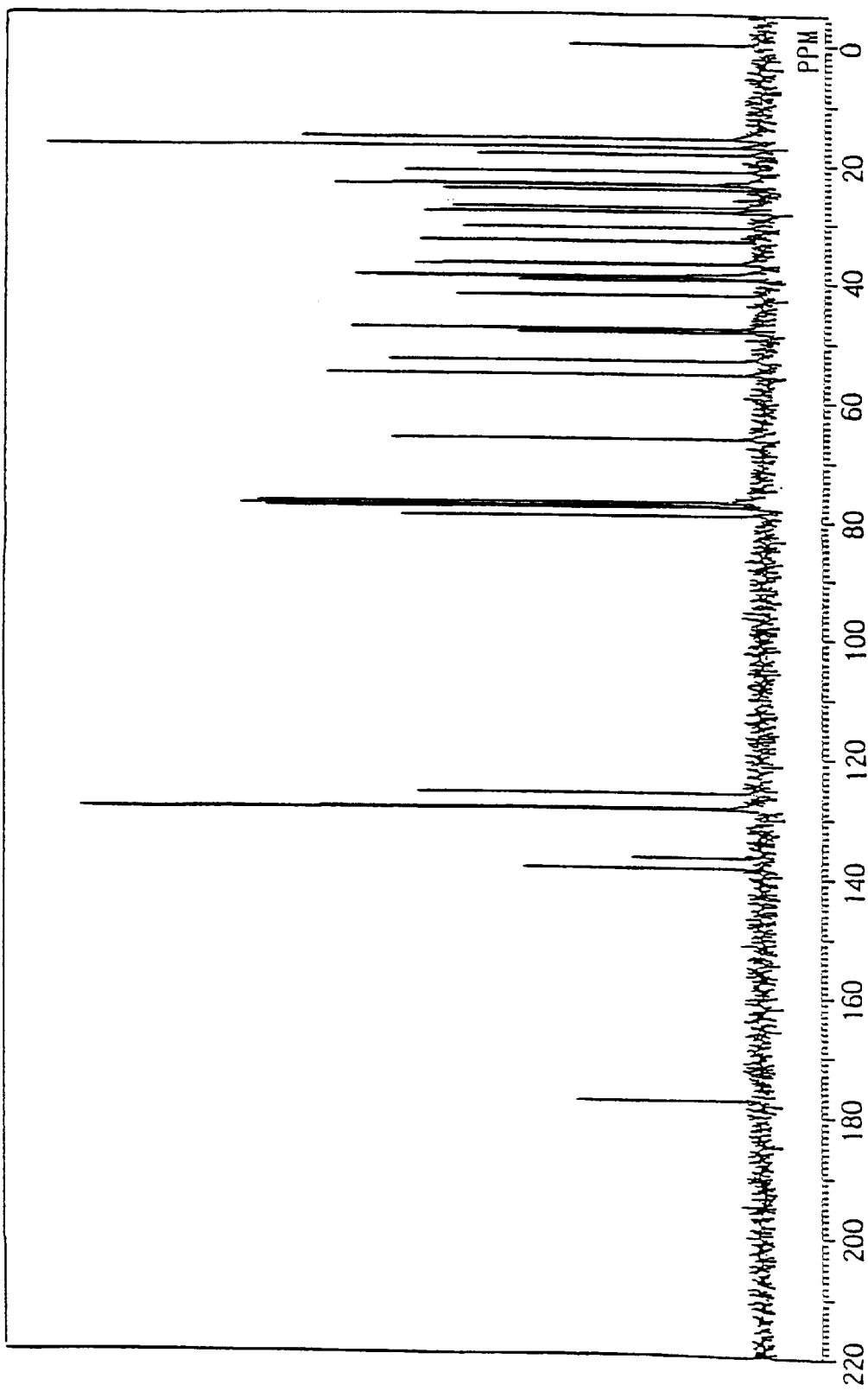
FIG. 2 is a chart illustrating results of $^{13}$C-NMR measurement of benzyl ursolate obtained in Production Example 1.
Figure 3:
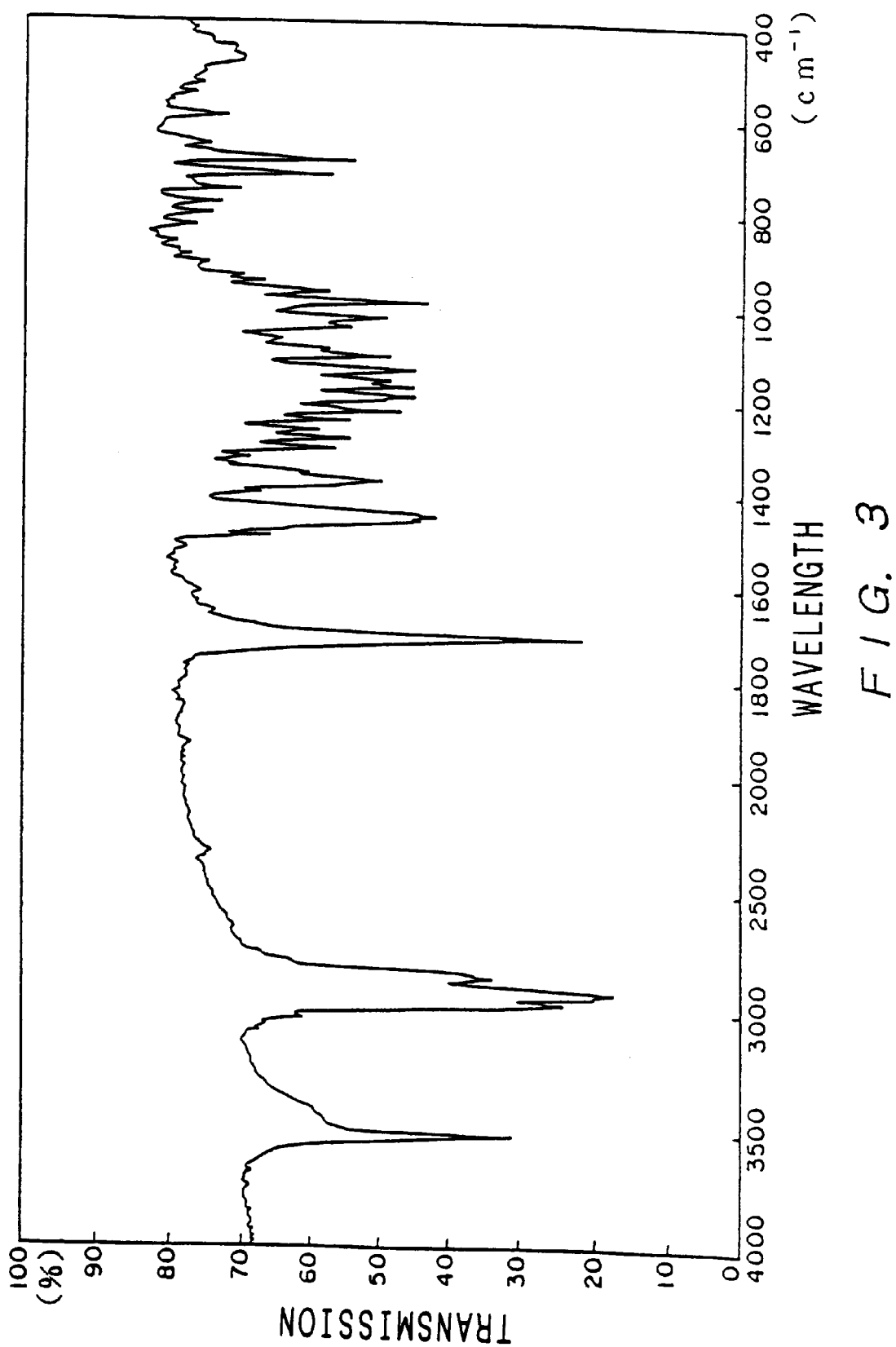
FIG. 3 is a chart illustrating results of IR measurement of benzyl ursolate obtained in Production Example 1.

Benzyl Ursolate and Benzyl Betulate 5 ml of benzyl bromide and 5 g of potassium carbonate were added to a solution obtained by dissolving 1 g of ursolic acid in 50 ml of acetone and the mixture was stirred at room temperature for one day and night under nitrogen atmosphere and then insoluble matter was filtered. After removing the solvent from the filtrate, the residue was purified through a silica gel column to obtain 1.2 g (yield 97%) of a benzyl derivative of ursolic acid. The obtained benzyl derivative of ursolic acid was measured by NMR (nuclear magnetic resonance) and IR (infrared spectrometry). The results obtained are illustrated in FIG. 1 relative to $^1$H-NMR, FIG. 2 relative to $^{13}$C-NMR, and FIG. 3 relative to IR. These results confirmed that the benzyl derivative of ursolic acid was benzyl ursolate having the structure which was derived by substituting a benzyl group for the hydrogen atom in the carboxyl group at the 28-position of ursolic acid.

The same synthetic method as described above was repeated except that 1 g of betulic acid was used instead of the ursolic acid to obtain 1.2 g (yield 97%) of benzyl betulate having the structure which was derived by substituting a benzyl group for the hydrogen atom in the carboxyl group at the 28-position of betulic acid.

PRODUCTION EXAMPLE 2

Methoxybenzyl Oleanolate 5 ml of benzyl bromide and 5 g of potassium carbonate were added to a solution obtained by dissolving 1 g of oleanolic acid in 50 ml of acetone and the mixture was stirred at room temperature for one day and night under nitrogen atmosphere and then insoluble matter was filtered. After removing the solvent from the filtrate, the residue was purified through a silica gel column to obtain 1.1 g (yield 84%) of methoxybenzyl oleanolate having the structure which was derived by substituting a methoxybenzyl group for the hydrogen atom in the carboxyl group at the 28-position of oleanolic acid.

PRODUCTION EXAMPLE 3

Nitrobenzyl Betulate and Nitrobenzyl Ursolate 5 ml of nitrobenzyl bromide and 5 g of potassium carbonate were added to a solution obtained by dissolving 1 g of betulic acid in 50 ml of acetone and the mixture was stirred at room temperature for one day and night under nitrogen atmosphere and then insoluble matter was filtered. After removing the solvent from the filtrate, the residue was purified through a silica gel column to obtain 1.1 g (yield 83%) of nitrobenzyl betulate having the structure which was derived by substituting a nitrobenzyl group for the hydrogen atom in the carboxyl group at the 28-position of betulic acid.

The same synthetic method as described above was repeated except that 1 g of ursolic acid was used instead of the betulic acid to obtain 1.05 g (yield 79%) of nitrobenzyl ursolate having the structure which was derived by substituting a nitrobenzyl group for the hydrogen atom in the carboxyl group at the 28-position of ursolic acid.

PRODUCTION EXAMPLE 4

Naphthylmethyl Ursolate and Naphthylmethyl Betulate 5 g of naphthylmethyl bromide and 5 g of potassium carbonate were added to a solution obtained by dissolving 1 g of ursolic acid in 50 ml of acetone and the mixture was stirred at room temperature for one day and night under nitrogen atmosphere and then insoluble matter was filtered. After removing the solvent from the filtrate, the residue was purified through a silica gel column to obtain 0.95 g (yield 72%) of naphthylmethyl ursolate having the structure which was derived by substituting a naphthylmethyl group for the hydrogen atom in the carboxyl group at the 28-position of ursolic acid.

The same synthetic method as described above was repeated except that 1 g of betulic acid was used instead of the ursolic acid to obtain 0.96 g (yield 73%) of naphthylmethyl betulate having the structure which was derived by substituting a naphthylmethyl group for the hydrogen atom in the carboxyl group at the 28-position of betulic acid.

PRODUCTION EXAMPLE 5

Diphenylmethyl Oleanolate 5 g of diphenylmethyl bromide and 5 g of potassium carbonate were added to a solution obtained by dissolving 1 g of oleanolic acid in 50 ml of acetone and the mixture was stirred at room temperature for one day and night under nitrogen atmosphere and then insoluble matter was filtered. After removing the solvent from the filtrate, the residue was purified through a silica gel column to obtain 1.05 g (yield 77%) of diphenylmethyl oleanolate having the structure which was derived by substituting a diphenylmethyl group for the hydrogen atom in the carboxyl group at the 28-position of oleanolic acid.

PRODUCTION EXAMPLE 6

Phenylbenzyl Betulate and Phenylbenzyl Oleanolate 5 g of methylbiphenyl bromide and 5 g of potassium carbonate were added to a solution obtained by dissolving 1 g of betulic acid in 50 ml of acetone and the mixture was stirred at room temperature for day and night under nitrogen atmosphere and then insoluble matter was filtered. After removing the solvent from the filtrate, the residue was purified through a silica gel column to obtain 1.1 g (yield 80%) of phenylbenzyl betulate having the structure which was derived by substituting a phenylbenzyl group for the hydrogen atom in the carboxyl group at the 28-position of betulic acid.

The same synthetic method as described above was repeated except that 1 g of oleanolic acid was used instead of the betulic acid to obtain 1.1 g (yield 80%) of phenylbenzyl oleanolate having the structure which was derived by substituting a phenylbenzyl group for the hydrogen atom in the carboxyl group at the 28-position of oleanolic acid.

PRODUCTION EXAMPLE 7

Benzoyl Oleanolate 1 g of oleanolic acid was dissolved in 50 ml of tetrahydrofuran and 3 g of triethylamine was added thereto to obtain a mixture solution. 1 g of benzoyl chloride was dripped to the mixture solution under ice cooling in a nitrogen atmosphere with stirring and then the mixture was stirred for 2 hours at room temperature. Thereafter, the reaction mixture was extracted with ethyl acetate and the extracted solution was treated with 2% aqueous hydrochloric acid solution, saturated sodium carbonate water, and sodium sulfate, respectively, followed by filtering to obtain a crude purification product. The crude purification product was further purified through a silica gel column to obtain 1.02 g of white crystals of benzoyl oleanolate which was the compound derived by substituting a benzoyl group for the hydrogen atom in the hydroxyl group bonded to the carbon atom at the 3-position of oleanolic acid. Yield was 80.5%.

PRODUCTION EXAMPLE 8

Methoxybenzoyl Betulate 1 g of betulic acid was dissolved in 50 ml of tetrahydrofuran and 3 g of triethylamine was added thereto to obtain a mixture solution. 1 g of methoxybenzoyl chloride was dripped to the mixture solution under ice cooling in a nitrogen atmosphere with stirring and then the mixture was stirred for 2 hours at room temperature. Thereafter, the reaction mixture was extracted with ethyl acetate and the extracted solution was treated with 2% aqueous hydrochloric acid solution, saturated sodium carbonate water, and sodium sulfate, respectively, followed by filtering to obtain a crude purification product. The crude purification product was further purified through a silica gel column to obtain 1 g of methoxybenzoyl betulate having the structure which was derived by substituting a methoxybenzoyl group for the hydrogen atom in the hydroxyl group bonded to the carbon atom at the 3-position of betulic acid. Yield was 76%.

PRODUCTION EXAMPLE 9

Phenylpropionyl Ursolate 1 g of ursolic acid was dissolved in 50 ml of tetrahydrofuran and 3 g of triethylamine was added thereto to obtain a mixture solution. 1 g of phenylpropionyl chloride was dripped to the mixture solution under ice cooling in a nitrogen atmosphere with stirring and then the mixture was stirred for 2 hours at room temperature. Thereafter, the reaction mixture was extracted with ethyl acetate and the extracted solution was treated with 2% aqueous hydrochloric acid solution, saturated sodium carbonate water, and sodium sulfate, respectively, followed by filtering to obtain a crude purification product. The crude purification product was further purified through a silica gel column to obtain 1.05 g of white crystals of phenylpropionyl ursolate which was the compound derived by substituting a phenylpropionyl group for the hydrogen atom in the hydroxyl group bonded to the carbon atom at the 3-position of ursolic acid. Yield was 78.1%.

PRODUCTION EXAMPLE 10

2-Ethylhexyl Benzylbetulate

A solution obtained by dissolving 11.9 g of thionyl chloride freshly distilled in 30 ml of benzene was dripped to a mixture solution obtained by dissolving 45.7 g of betulic acid and 10.1 g of triethylamine in 100 ml of benzene under ice cooling with one-hour stirring for reaction. A mixture solution obtained by dissolving 12 g of 2-ethylhexyl alcohol and 10.1 g of triethylamine in 30 ml of benzene was dripped to the reaction mixture without removing the resulting betulic chloride therefrom under ice cooling and the reaction was continued for 3 hours. Thereafter, the resulting triethylamine hydrochloride was filtered and the solvent was distilled off at 40° C. or less to obtain 2-ethylhexyl betulate. The 2-ethylhexyl betulate thus obtained was dissolved in 200 ml of benzene and 32 g of triethylamine was added thereto. 30 ml of benzyl bromide was dripped to the obtained mixture solution under ice cooling with one-hour stirring for reaction. Then, the mixture was stirred for 2 hours at room temperature and then refluxed at the boiling temperature of benzene for 1 hour. After the reaction was stopped, unreacted triethylamine was treated with 2% hydrochloric acid, and then the reaction product was extracted with ethyl acetate. Then, the extraction solvent was distilled off from the extract to obtain a crude purification product. Further purification was performed using a column by eluting with hexane/ether (9/1) solvent to obtain 32 g of colorless liquid of 2-ethylhexyl benzylbetulate which was the compound derived by substituting a benzyl group for the hydrogen atom in the hydroxyl group bonded to the carbon atom at the 3-position of 2-ethylhexyl betulic acid. Yield was 50%.

<Evaluation of the Photoaging Inhibitors of the Present Invention>

With respect to the triterpenoid compound obtained in Production Examples described above, safety and photoaging inhibiting effects for the skin are tested in accordance with the following processes, serving the evaluation of the photoaging inhibitors of the present invention.

(1) Safety Tests (1)-1. Skin Irritation Test

Skin irritation tests of benzyl ursolate, methoxybenzyl oleanolate, nitrobenzyl betulate, naphthylmethyl ursolate, diphenylmethyl oleanolate, benzoyl oleanolate, methoxybenzoyl betulate, and phenylpropionyl ursolate obtained in the above-described Production Examples were made using Hartley guinea pigs (300 to 500 g, female) as test animals.

For test groups each consisting of 6 guinea pigs, the hair on the back of each guinea pig was removed or shaven and on the hair-removed or shaven portion was applied a plastic adhesive plaster which a cloth patch of 15 mm in diameter impregnated with 50 mg of white vaseline containing a 10% by weight of one of the aromatic compound derivatives of triterpenoid obtained in the Production Examples described above was attached, and then 24 hours' closed patch test was performed. After the closed patch tests were completed, the resulting skin reactions after the removal of the plastic adhesive plasters were evaluated immediately (after 0 hour) and after 24 hours respectively, according to the evaluation criteria below and an average score was calculated based on the results obtained 6 animals in each test group.

(Evaluation Criteria)

0: No skin reaction being observed

1: Weak or unclearly bordered erythema

2: Clear erythema

3: Reaction accompanying edema

4: Reaction of ulcer, necrosis, or the like

As a control, the above-described test and evaluation were conducted with only white vaseline. Table 1 shows the results.

TABLE 1

| Name of Compound | Score (Average) | |
|---|---|---|
| | After 0 hour | After 24 hours |
| Benzyl ursolate | 0 | 0 |
| Methoxybenzyl oleanolate | 0 | 0 |
| Nitrobenzyl betulate | 0 | 0 |
| Naphthylmethyl ursolate | 0 | 0 |
| Diphenylmethyl oleanolate | 0 | 0 |
| Benzoyl oleanolate | 0 | 0 |
| Methoxybenzoyl betulate | 0 | 0 |
| Phenylpropionyl ursolate | 0 | 0 |
| Control (white vaseline only) | 0 | 0 |

(1)-2. Allergy Test

Allergy tests of benzyl ursolate, methoxybenzyl oleanolate, phenylbenzyl betulate, benzoyl oleanolate, methoxybenzoyl betulate, and phenylpropionyl ursolate obtained in the above-described Production Examples were made using Hartley guinea pigs (300 to 500 g, female) as test animals.

For test groups each consisting of 6 guinea pigs were applied each an aromatic compound derivative of triterpenoid to a concentration of 3 w/v % in olive oil, an aromatic compound derivative of triterpenoid to a concentration of 0.3 w/v % in olive oil, and neat olive oil, respectively, by a maximization method to perform sensitization induction.

Thereafter, in order to induce sufficient immunoresponse, after a grace period of 10 days from the day when the final sensitization was made, there was applied to the back skin of each guinea pig a patch plate having 1.5 cm diameter coated with 100 μl of an aromatic compound derivative of triterpenoid to a concentration of 3 w/v % in olive oil, an aromatic compound derivative of triterpenoid to a concentration of 0.3 w/v % in olive oil, or neat olive oil, and the patch plate was removed after 24 hours. The resulting skin reaction after 24 hours from the removal of the patch plate was evaluated according to the following evaluation criteria and an average score was calculated for each test group. Table 2 shows the results.

(Evaluation Criteria)
 0: No skin reaction being observed
 1: Weak or unclearly bordered erythema
 2: Clear erythema
 3: Reaction accompanying edema
 4: Reaction of ulcer, necrosis, or the like

TABLE 2

| Name of Compound | | Evaluation Score (Average) | | |
|---|---|---|---|---|
| | | 3%-induced group | 0.3%-induced group | Olive oil induced group |
| Benzyl ursolate | 3%-sensitized group | 0.17 | 0 | 0.33 |
| | 0.3%-sensitized group | 0 | 0.17 | 0 |
| | Olive oil-sensitized group | 0 | 0 | 0.17 |
| Methoxybenzyl oleanolate | 3%-sensitized group | 0.33 | 0 | 0.17 |
| | 0.3%-sensitized group | 0 | 0 | 0.17 |
| | Olive oil-sensitized group | 0.17 | 0.17 | 0 |
| Phenylbenzyl betulate | 3%-sensitized group | 0.17 | 0.17 | 0.17 |
| | 0.3%-sensitized group | 0 | 0 | 0 |
| | Olive oil-sensitized group | 0 | 0 | 0.17 |
| Benzoyl oleanolate | 3%-sensitized group | 0 | 0 | 0 |
| | 0.3%-sensitized group | 0 | 0 | 0 |
| | Olive oil-sensitized group | 0 | 0 | 0 |
| Methoxybenzoyl betulate | 3%-sensitized group | 0.17 | 0 | 0.17 |
| | 0.3%-sensitized group | 0 | 0.17 | 0 |
| | Olive oil-sensitized group | 0 | 0 | 0.17 |
| Phenylpropionyl ursolate | 3%-sensitized group | 0 | 0 | 0 |
| | 0.3%-sensitized group | 0.17 | 0 | 0 |
| | Olive oil-sensitized | 0 | 0 | 0 |

From these results, it is apparent that the triterpenoid compounds obtained in the above-described Production Examples each cause substantially no skin irritation nor allergy so that the photoaging inhibitor of the present invention can be said to be excellent in safety.

(2) UV Wrinkle Model Amelioration Test

UV wrinkle model amelioration tests were conducted with the benzyl ursolate, methoxybenzyl oleanolate, phenylbenzyl betulate, benzoyl oleanolate, methoxybenzoyl betulate, and phenylpropionyl ursolate obtained in the above described Production Examples on hairless mice (5-week old, female) as test animals.

UVB (60 mJ/cm$^2$) was irradiated to the back skin of each animal of a test group consisting of 10 hairless mice once a day in a frequency of 5 days a week and after 8 weeks formation of wrinkles on the back skin due to photoaging was confirmed. Thereafter, 100 μl of ethanol solutions containing the aromatic compound derivatives of triterpenoid obtained in the Production Examples in concentrations shown in Table 3 were applied thereon once a day in a frequency of 5 days a week. After 9 weeks from the initiation of applying, the degree of ameliorating wrinkles in the skin due to photoaging were evaluated with naked eyes according to the following evaluation criteria.

(Evaluation Criteria)
 −: No wrinkle-ameliorating effect was observed.
 ±: Slight wrinkle-ameliorating effect was observed.
 +: Wrinkle-ameliorating effect was observed.

For comparison, ethanol solutions containing of palmitoyl oleanolate or 2-ethylhexyl 2-ethylhexanoyl ursolate in 1% concentration, hitherto used as drugs having a photoaging inhibiting effect, and neat ethanol as a control were applied to hairless mice after UVB irradiation in the same manner as described above and wrinkle-ameliorating effects were evaluated, respectively. Table 3 shows the results.

TABLE 3

| Sample | | | | |
|---|---|---|---|---|
| Name of Compound | concen-tration (w/v %) | Number of Mice (number) + | ± | − |
| Benzyl ursolate | 0.005 | 9 | 1 | 0 |
| Methoxybenzyl oleanolate | 0.01 | 7 | 3 | 0 |
| Phenylbenzyl betulate | 0.05 | 8 | 2 | 0 |
| Benzoyl oleanolate | 0.01 | 6 | 4 | 0 |
| Methoxybenzoyl betulate | 0.01 | 8 | 2 | 0 |
| Phenylpropionyl ursolate | 0.05 | 7 | 3 | 0 |
| Palmitoyl oleanolate | 1.0 | 7 | 3 | 0 |
| 2-Ethylhexyl 2-ethylhexanoyl ursolate | 1.0 | 6 | 4 | 0 |
| Control (ethanol only) | — | 0 | 2 | 8 |

From these results, it is apparent that the aromatic compound derivatives of triterpenoid obtained by the Production Examples described above exhibit sufficient wrinkled skin ameliorating effect when administered in very low concentrations (concentrations of about 1/20 to about 1/200) as compared the triterpenoid derivatives which are derived by acylating the hydroxyl group bonded to the carbon atom at the 3-position of ursolic, oleanolic or betulic acid with an aliphatic compound and/or by esterifying the carboxyl group at the 28-position of the acid with an aliphatic compound, such as palmitoyl oleanolate and 2-ethylhexyl 2-ethylhexanoyl ursolate which are conventionally used, so that the photoaging inhibitor of the present invention has an excellent photoaging inhibiting effect.

Next, examples of the skin-care preparations containing the aromatic compound derivatives of triterpenoid obtained in the above-described Production Examples. Note that the blending amounts used below are all part by weight.

EXAMPLE 1

Skin Lotion

Components A shown in Table 4 were dissolved each other at room temperature and a solution of components B separately dissolved each other at room temperature were added thereto to solubilize, thus a skin lotion containing the benzyl ursolate obtained in Production Example 1 was produced. Similarly, a skin lotion of the comparative example was produced which contains hitherto used triterpenoid derivative i.e. octanoyl ursolate instead of benzyl ursolate.

TABLE 4

| | Blending Amount (Part by Weight) | |
|---|---|---|
| Component | Example 1 | Comparative Example 1 |
| A Ethanol | 8.0 | 8.0 |
| Benzyl ursolate of Production Example 1 | 0.05 | — |
| Octanoyl ursolate | — | 1.0 |
| 1,3-Butylene glycol | 6.0 | 6.0 |
| Glycerol | 3.0 | 3.0 |
| Polyoxyethylene(20) oleyl ether | 0.5 | 0.5 |

TABLE 4-continued

| | Blending Amount (Part by Weight) | |
|---|---|---|
| Component | Example 1 | Comparative Example 1 |
| B Methylparaben | 0.1 | 0.1 |
| Perfume | 0.05 | 0.05 |
| Citric acid | 0.1 | 0.1 |
| Sodium citrate | 0.15 | 0.15 |
| Purified water | 82.05 | 81.1 |

EXAMPLE 2

Emulsion

Components A in Table 5 were mixed with heating at 70° C. Separately, components B were mixed with heating at 70° C. The components A were added to the components B and emulsified and while cooling the component C was added thereto to produce an emulsion containing the methoxybenzyl oleanolate obtained in Production Example 2 above. Similarly, a comparative example skin lotion was produced which contains hitherto used triterpenoid derivative i.e. ethyl palmitoyloleanolate instead of methoxybenzyl oleanolate.

TABLE 5

| | Blending Amount (Part by Weight) | |
|---|---|---|
| Component | Example 2 | Comparative Example 2 |
| A Squalane | 3.5 | 3.5 |
| Paraffin wax 130 | 1.0 | 1.0 |
| Hydrogenated beef tallow | 1.3 | 1.3 |
| Cholesteryl hydroxystearate | 0.65 | 0.65 |
| Stearic acid monoglyceride | 3.0 | 3.0 |
| Oleic acid triglyceride | 7.5 | 7.5 |
| Stearic acid | 1.5 | 1.5 |
| Methoxybenzyl oleanolate of Production Example 2 | 0.05 | — |
| Ethyl palmitoyloleanolate | — | 0.5 |
| B Glycerol | 10.0 | 10.0 |
| Dipropylene glycol | 5.0 | 5.0 |
| PEG-1500 | 1.0 | 1.0 |
| Sodium hydroxide | 0.2 | 0.2 |
| Ethylparaben | 0.2 | 0.2 |
| Purified water | 64.9 | 64.45 |
| C Perfume | 0.2 | 0.2 |

EXAMPLE 3

Cream

Components A in Table 6 were mixed with heating at 70° C. and components B separately mixed with heating at 70° C. were added thereto, and the mixture was emulsified and cooled to 35° C. The component C was further added to the emulsified mixture to produce a cream containing the naphthylmethyl betulate obtained in Production Example 4 above.

TABLE 6

| Component | Blending Amount |
|---|---|
| A Squalane | 11.0 |
| Jojoba oil | 8.0 |

TABLE 6-continued

| Component | Blending Amount |
|---|---|
| Docosane glycol isostearate | 3.0 |
| Glyceryl tri-2-ethylhexanoate | 5.0 |
| Dicapric acid neopentyl glycol | 4.5 |
| Stearyl alcohol | 2.0 |
| Hydrogenated palm nut oil | 1.5 |
| Stearic acid | 1.0 |
| Polyoxyethylene(5)stearic acid monoglyceride | 1.1 |
| Stearic acid monoglyceride | 3.0 |
| Naphthylmethyl betulate of Production Example 4 | 0.01 |
| B Ethylparaben | 0.3 |
| Potassium hydroxide | 0.03 |
| Propylene glycol | 5.0 |
| Dipropylene glycol | 4.0 |
| Purified water | 50.36 |
| C Perfume | 0.2 |

EXAMPLE 4

Cream

Components A in Table 7 were mixed with heating at 80° C. and components B separately mixed with heating at 80° C. were added thereto, and the mixture was stirred and emulsified, and then cooled to 35° C. to produce a cream containing the benzyl betulate obtained in Production Example 1 above.

TABLE 7

| Component | Blending Amount (Part by Weight) |
|---|---|
| A Squalane | 10.0 |
| Cholesteryl isostearate | 7.0 |
| Cholesterol | 1.2 |
| Butyl alcohol | 1.0 |
| Jojoba oil | 3.6 |
| Dicapric acid neopentyl glycol | 8.5 |
| Myristic acid triglyceride | 1.7 |
| Stearic acid diglyceride | 1.5 |
| Isostearic acid diglyceride | 1.0 |
| Sphingolipid | 2.3 |
| Cetostearyl alcohol | 0.3 |
| Myristic acid | 2.0 |
| Stearic acid | 2.5 |
| POE(10)methyl glucoside | 4.0 |
| 2-Hydroxy-4-methoxybenzophenone | 0.5 |
| Tocopherol acetate | 0.1 |
| Methylparaben | 0.4 |
| Ethylparaben | 0.2 |
| Butylparaben | 0.1 |
| Benzyl betulate of Production Example 1 | 0.01 |
| B Purified water | 36.32 |
| 1,3-Butylene glycol | 2.15 |
| Glycerol | 13.6 |
| Sodium hydroxide | 0.01 |
| Potassium hydroxide | 0.01 |

EXAMPLE 5

Emulsion

Components A and components B in Table 8 were dissolved at 70° C. with stirring separately and then the components A were added to the components B to carry out preemulsification. Next, the preemulsion was homogeneously emulsified using a homomixer, followed by cooling to 30° C. with stirring to produce an emulsion containing phenylbenzyl oleanolate obtained in Production Example 6.

TABLE 8

| Component | Blending Amount (Part by Weight) |
|---|---|
| A Synthetic spermaceti | 2.5 |
| Cetanol | 1.0 |
| Macadamia nut oil | 4.0 |
| Stearic acid | 1.0 |
| Polyethylene glycol monostearate (25EO) | 2.2 |
| Stearic acid monoglyceride | 0.5 |
| Butylparaben | 0.1 |
| γ-Tocopherol | 0.05 |
| BHT | 0.01 |
| 4-(1,1-Dimethylethyl)-4'-methoxy-dibenzoylmethane | 0.5 |
| B 1,3-Butylene glycol | 3.0 |
| Propylene glycol | 7.0 |
| Xanthan gum | 0.1 |
| Carboxyvinyl polymer | 0.2 |
| Potassium hydroxide | 0.2 |
| Phenylbenzyl oleanolate of Production Example 6 | 0.005 |
| Purified water | 77.635 |

EXAMPLE 6

Skin Lotion

Components A shown in Table 9 were dissolved each other at room temperature and then the components B separately dissolved each other at room temperature were added thereto to solubilize, thus a skin lotion containing nitrobenzyl ursolate obtained in Production Example 3 above was produced.

TABLE 9

| Component | Blending Amount (Part by Weight) |
|---|---|
| A POE(20) Octyl dodecyl ether | 0.3 |
| Tocopherol | 0.02 |
| Nitrobenzyl ursolate of Production Example 3 | 0.005 |
| B Glycerol | 4.0 |
| Ethanol | 7.5 |
| Propylene glycol | 3.4 |
| PEG-1500 | 2.5 |
| Maltitol | 0.8 |
| Sodium isoferulate | 0.5 |
| Citric acid | 0.15 |
| Sodium citrate | 0.1 |
| Purified water | 80.725 |

<Evaluation of the Skin-care Preparation of the Present Invention>

Practical use tests were conducted using the skin-care preparations obtained in Examples 1 and 2 and Comparative Examples 1 and 2 to evaluate the skin beautifying effect of the skin-care preparations of the present invention.

Twenty Japanese male volunteers with clear wrinkles in the corner of the eye as panelists, divided into two groups each containing 10 persons, participated in the tests i.e. half face tests. Before the tests, the faces of all the panelists were photographed. Thereafter, the skin lotion of Example 1 was applied to one corner of the eye in one half face of each panelist in Group A, and the skin lotion of Comparative Example 1 was applied to the other corner of the eye. On the other hand, the emulsion of Example 2 was applied to one corner of the eye of each panelist in Group B, and the emulsion of Comparative Example 2 was applied to the other corner of the eye. Every skin-care preparation described-above was applied twice a day for continuous 6 weeks by an ordinary method. After 6 weeks from the initiation of the application, the states of wrinkles amelioration and natural aggravation were evaluated with the following evaluation criteria by comparing the states before use and after 6 weeks of use using the above-described photographs in the group. Table 10 shows the results.

(Evaluation Criteria)

+++: Prominent amelioration

++: Considerable amelioration

+: Slight amelioration

−: No change

−−: Natural aggravation

TABLE 10

| Group | Skin-care Preparation | Number of Panelist (Number) | | | | |
|---|---|---|---|---|---|---|
| | | +++ | ++ | + | − | −− |
| A | Example 1 | 6 | 2 | 1 | 1 | 0 |
| | Comparative Example 1 | 6 | 1 | 2 | 1 | 0 |
| B | Example 2 | 7 | 2 | 1 | 0 | 0 |
| | Comparative Example 2 | 6 | 2 | 1 | 1 | 0 |

From the results, it can be seen that the skin-care preparations of the Examples containing the aromatic compound derivatives of triterpenoid gained excellent evaluation with respect to wrinkle-ameliorating effect. Also, it was confirmed that the skin-care preparations of the Comparative Examples containing the hitherto used triterpenoid derivatives such as octanoyl ursolate or ethyl palmitoyloleanolate in concentrations 10 times or more as those of the aromatic compound derivatives of triterpenoid in the skin-care preparations of the present invention exhibit equivalent wrinkle-ameliorating effect to that of the skin-care preparations of the present invention. At the same time, it has been confirmed that the skin-care preparations of the present invention are substantially free of harmful effect on the touch, such as stickiness and the like.

INDUSTRIAL APPLICABILITY

The photoaging inhibitors of the present invention is highly safe and excellent in photoaging inhibiting effect as compared with the conventional triterpenoid compounds so that when they are blended to a composition, they can exhibit sufficient photoaging inhibiting effect in small blending amounts. Further, the skin-care preparations of the present invention not only are excellent in the skin beautifying effect such as the inhibiting or ameliorating effect to wrinkled skin and the like but also can be used safely without evil effects to the skin.

What is claimed is:

1. A compound selected from triterpenoid derivatives and salts thereof, wherein the triterpenoid derivatives are derived by substituting a general formula (I) listed below for a hydrogen atom in a carboxyl group at the 28-position of ursolic, oleanolic or betulic acid,

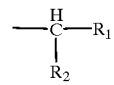

wherein, in the above formula (I), $R_1$ represents a phenyl group, a methoxyphenyl group, an ethoxyphenyl group, a butoxyphenyl group, a nitrophenyl group, a diphenyl group, or a naphthyl group and $R_2$ represents a hydrogen atom or a phenyl group.

2. A compound as claimed in claim 1, wherein, in the general formula (I), $R_1$ represents a phenyl group, a methoxyphenyl group, an ethoxyphenyl group, a butoxyphenyl group, a nitrophenyl group, a diphenyl group, or a naphthyl group, and $R_2$ represents a hydrogen atom.

3. A compound as claimed in claim 1, wherein, in the general formula (I), $R_1$ represents a phenyl group and $R_2$ represents a phenyl group.

4. A compound selected from triterpenoid derivatives and salts thereof, wherein the triterpenoid derivatives are derived by substituting a general formula (II) listed below for a hydrogen atom in a hydroxyl group bonded to a carbon atom at the 3-position of ursolic, oleanolic or betulic acid,

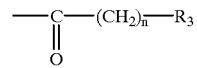

wherein, in the above formula (II), n represents 0 or an integer of up to 2, and $R_3$ represents a phenyl group, a methoxyphenyl group, an ethoxyphenyl group, a butoxyphenyl group, a nitrophenyl group, a diphenyl group, or a naphthyl group.

5. A compound as claimed in claim 4, wherein, in the general formula (II), n represents 0 or an integer of up to 2, and $R_3$ represents a phenyl group, a methoxyphenyl group, an ethoxyphenyl group, or a butoxyphenyl group.

6. A compound selected from triterpenoid derivatives and salts thereof, wherein the triterpenoid derivatives are derived by substituting a general formula (III) listed below for a hydrogen atom in a hydroxyl group bonded to a carbon atom at the 3-position of ursolic, oleanolic or betulic acid,

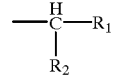

wherein in the above formula (III), $R_1$ represents a phenyl group, a methoxyphenyl group, an ethoxyphenyl group, or a butoxyphenyl group, and $R_2$ represents a hydrogen atom.

7. A method of treating wrinkled skin comprising applying to the wrinkled skin an effective amount of a composition comprising at least one triterpenoid derivative and salts thereof according to claim 1.

8. A method of treating wrinkled skin comprising applying to the wrinkled skin effective amount of a composition comprising at least one triterpenoid derivative and salts thereof according to claim 4.

9. A method of treating wrinkled skin comprising applying to the wrinkled skin an effective amount of a composition comprising at least one triterpenoid derivative and salts thereof according to claim 6.

* * * * *